(12) United States Patent  (10) Patent No.: US 8,287,460 B2
Broadley et al.  (45) Date of Patent: Oct. 16, 2012

(54) DISORDERED BREATHING MONITORING DEVICE AND METHOD OF USING SAME INCLUDING A STUDY STATUS INDICATOR

(75) Inventors: William H. Broadley, Pittsburgh, PA (US); Richard J. Lordo, Butler, PA (US); Ronald D Fligge, Greensburg, PA (US); Daniel Martin, Delmont, PA (US); Duane H Carter, Irwin, PA (US); Steven J Albright, Delmont, PA (US)

(73) Assignee: RIC Investments, LLC, Wilmington, DE (US)

( * ) Notice: Subject to any disclaimer, the term of this patent is extended or adjusted under 35 U.S.C. 154(b) by 650 days.

(21) Appl. No.: 12/101,486

(22) Filed: Apr. 11, 2008

(65) Prior Publication Data

US 2009/0099471 A1  Apr. 16, 2009

Related U.S. Application Data

(63) Continuation-in-part of application No. 11/542,475, filed on Oct. 3, 2006, now abandoned.

(60) Provisional application No. 61/037,750, filed on Mar. 19, 2008, provisional application No. 60/723,539, filed on Oct. 4, 2005.

(51) Int. Cl.
*A61B 5/08* (2006.01)
(52) U.S. Cl. .......................... 600/538; 600/529; 600/301
(58) Field of Classification Search .......... 600/531–538, 600/529, 300–301
See application file for complete search history.

(56) References Cited

U.S. PATENT DOCUMENTS

| 4,802,485 A * | 2/1989 | Bowers et al. ............... 600/324 |
|---|---|---|
| 5,203,343 A | 4/1993 | Axe et al. |
| 5,259,373 A | 11/1993 | Gruenke et al. |
| 5,295,490 A | 3/1994 | Dodakian |
| 5,355,893 A | 10/1994 | Mick et al. |
| 5,458,137 A | 10/1995 | Axe et al. |
| 5,520,176 A | 5/1996 | Cohen |
| 5,540,733 A | 7/1996 | Testerman et al. |
| 5,555,891 A | 9/1996 | Eisenfeld |
| 5,605,151 A | 2/1997 | Lynn |
| 5,671,733 A | 9/1997 | Raviv et al. |
| 5,797,852 A | 8/1998 | Karakasoglu et al. |
| 5,800,360 A | 9/1998 | Kisner et al. |
| 5,832,592 A | 11/1998 | Bowman et al. |
| 5,879,313 A | 3/1999 | Raviv et al. |

(Continued)

OTHER PUBLICATIONS

Shocat et al., "The SleepStrip™: an apnoea screener for the early detection of sleep apnoea syndrome", European Respiratory Journal, 2002, pp. 121-126, United Kingdom.

(Continued)

*Primary Examiner* — Michael Kahelin
*Assistant Examiner* — Michael D'Angelo

(57) ABSTRACT

An apparatus and associated method for collecting data for a sleep study. The apparatus includes a sensor adapted to collect data relating to a parameter of a user of the apparatus over a period of time, and a controller operatively coupled to the sensor. The controller is adapted to: (a) receive configuration information specifying a predetermined amount of valid data that is required for a sleep study to be deemed valid, (b) receive the data relating to the parameter and determine an amount of the received data that is valid, and (c) cause a study status indicator to be output by the apparatus based on the amount of the received data that is determined to be valid and the predetermined amount specified in the configuration information.

25 Claims, 9 Drawing Sheets

U.S. PATENT DOCUMENTS

| | | | |
|---|---|---|---|
| 5,961,447 A | | 10/1999 | Raviv et al. |
| 5,989,193 A | | 11/1999 | Sullivan |
| 6,062,216 A | * | 5/2000 | Corn .................... 128/204.23 |
| 6,085,747 A | | 7/2000 | Axe et al. |
| 6,091,973 A | | 7/2000 | Colla et al. |
| 6,120,441 A | | 9/2000 | Griebel |
| 6,138,675 A | | 10/2000 | Berthon-Jones |
| 6,142,950 A | | 11/2000 | Allen et al. |
| 6,165,133 A | | 12/2000 | Rapoport et al. |
| 6,171,258 B1 | | 1/2001 | Karakasoglu et al. |
| 6,213,955 B1 | | 4/2001 | Karakasoglu et al. |
| 6,306,088 B1 | | 10/2001 | Krausman et al. |
| 6,368,287 B1 | | 4/2002 | Hadas |
| 2003/0066529 A1 | | 4/2003 | Truschel et al. |
| 2005/0119711 A1 | * | 6/2005 | Cho et al. .................... 607/42 |

OTHER PUBLICATIONS

S.L.P. LTD., "SleepStrip® Disposable Sleep Apnea Screener", product brochure, 2002.
Respironics, Inc., "Night Owl™ Pocket Polygraph Operator's Manual", 1996.
Sector Medical, "The APLAB Product and Obstructive Sleep Apnea Syndrome", product brochure, 2004.
Sleep Solutions, "Instructions for Use Bedbugg", 2000.
Sleep Solutions, "NovaSomQSG Technology Summary",2002.
SOMTE PSG, Product Description. 2007.
Grass Telefactor, "SleepTrek, Portable Sleep Screener", 2006.
Medcare, "Smart Sleep System, Embella" product literature, 2007.
Puritan Bennett, "Sandman Pocket Portable Recorder", 2007.

* cited by examiner

DISORDERED BREATHING MONITORING DEVICE AND METHOD OF USING SAME INCLUDING A STUDY STATUS INDICATOR

CROSS-REFERENCE TO RELATED APPLICATIONS

This application is a Continuation-In-Part (CIP) of U.S. application Ser. No. 11/542,475, entitled "Disordered Breathing Monitoring Device and Method of Using Same," filed on Oct. 3, 2006, which claims the benefit of U.S. provisional application No. 60/723,539, filed on Oct. 4, 2005, the disclosures of both of which are incorporated herein by reference. This application also claims the benefit of U.S. provisional application No. 61/037,750, entitled "Good Sleep Study Indicator and Associated Method," filed on Mar. 19, 2008, the disclosure of which is incorporated herein by reference.

BACKGROUND OF THE INVENTION

1. Field of the Invention

The present invention relates to diagnosing and screening for sleep disorders, such as obstructive sleep apnea (OSA), and, in particular, to an apparatus and a method for collecting data for a sleep study for diagnosing and screening for a sleep disorder wherein a status indicator is provided to indicate to the user whether enough valid data for the study has been collected.

2. Description of the Related Art

Obstructive sleep apnea (OSA) is a condition in which sleep is repeatedly interrupted by an inability to breathe due to an obstructed upper airway segment. Those afflicted with OSA experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of OSA include right ventricular dysfunction, carbon dioxide retention during wakefulness, as well as during sleep, and continuous reduced arterial oxygen tension. Hypersomnolent sleep apnea patients may be at risk for excessive mortality from these factors as well as by an elevated risk for accidents while driving and/or operating potentially dangerous equipment.

OSA can only be diagnosed by a sleep study. A sleep study may be performed at a sleep lab using sophisticated equipment under the direction of a clinician. Such studies are commonly referred to as an "attended" sleep studies due to the presence of the clinician. Some people, however, find it difficult to sleep when hooked up to the numerous wires and sensors required by the sleep lab equipment and/or under the watchful eye of a clinician. Alternatively, a sleep study may be conducted by a patient outside of a sleep lab (commonly referred to as an "unattended" sleep study) using a portable data recorder that collects data relating to certain parameters of the patient while the patient is sleeping (typically overnight). The collected data is then used by a clinician to determine whether the patient has OSA.

A proper sleep study requires that a certain amount of valid data be collected from the patient. In addition, Medicare reimbursement guidelines define a "Sleep Study" to be: "simultaneous recording of ventilation, respiratory effort, ECG or heart rate, and oxygen saturation" while "attended" or "unattended" by a "technologist." The guidelines also state that "[s]leep studies and polysomnography refer to the continuous and simultaneous monitoring and recording of various physiological and pathophysiological parameters of sleep for 6 or more hours with physician review, interpretation and report." These guidelines are used by most private payors as well. In the case of an unattended study, in order to assess whether enough valid, quality data has been collected during the study, the data must be downloaded from the portable data recorder that was used to a clinician's external computer so that it can be analyzed.

Current portable data recorders, however, typically offer limited feedback to the patient. Thus, if a sleep study is conducted unattended in a patient's home, the patient will not know whether sufficient valid data has been recorded until the portable data recorder is returned to the clinician and the data is analyzed. If the recorded data is not sufficient/acceptable, the portable data recorder must be reconfigured and returned to the patient so that another study can be performed. This process will be time consuming and inconvenient to the patient and may discourage the patient from taking the time required to complete a valid sleep study. In addition, the need to repeat sleep studies due to insufficient data places an additional financial burden on the healthcare system. Thus, there is a need for an apparatus that determines whether sufficient valid data has been collected during a study and provides an indication thereof to the patient.

SUMMARY OF THE INVENTION

The present invention provides, in one non-limiting embodiment, an apparatus for collecting data for a sleep study that includes a sensor adapted to collect data relating to a parameter of a user of the apparatus over a period of time, and a controller operatively coupled to the sensor. The controller is adapted to: (a) receive configuration information specifying a predetermined amount of valid data that is required for a sleep study to be deemed valid, (b) receive the data relating to the parameter and determine an amount of the received data that is valid, and (c) cause a study status indicator to be output by the apparatus based on the amount of the received data that is determined to be valid and the predetermined amount specified in the configuration information. The study status indicator may be representative of a percentage based on the amount of the received data that is determined to be valid as compared to the predetermined amount specified in the configuration information. The study status indicator may also be a visual indicator that includes a plurality of sections, wherein at least one section in the plurality of sections is visually distinguished from a remainder of the plurality of sections based on the percentage.

In one particular embodiment, the sensor comprises a flow sensor adapted to collect flow data relating to a flow of gas breathed in and out by the user, and the apparatus further comprises an oximetry sensor adapted to collect oximetry data relating to an oxygen saturation of the user, wherein the data relating to the parameter comprises the flow data and the oximetry data, and wherein the controller is adapted to determine an amount of the received data that is valid by determining an accumulated time during which the flow data and the oximetry data are simultaneously valid.

The oximetry sensor may comprise an SpO2 probe. Also, the flow sensor may comprise a temperature sensor adapted to collect the flow data based on a temperature of the gas breathed in and out by the user, a pressure transducer adapted to collect the flow data based on pressure variations of the gas breathed in and out by the user, or both the temperature sensor and the pressure transducer.

In another particular embodiment, the flow data is deemed to be valid responsive to a peak-to-peak change in the flow data exceeding a predetermined threshold. Also, portions of the flow data and the oximetry data may be deemed to be simultaneously valid during time periods where both the flow data and the oximetry data are valid for at least a predetermined amount of time.

The present invention also provides, in another non-limiting embodiment, a method of collecting data for a sleep study that includes receiving configuration information specifying a predetermined amount of valid data that is required for a sleep study to be deemed valid, collecting data relating to a parameter of a patient over a period of time, determining an amount of the collected data that is valid, storing at least the collected data that is determined to be valid, and providing a study status indicator based on the amount of the collected data that is determined to be valid and the predetermined amount specified in the configuration information. In addition to displaying the study status, this status information may also be stored in a text file created for each study so that it may later be accessed by a clinician.

The step of collecting data relating to the parameter may comprise collecting flow data relating to a flow of gas breathed in and out by the user, and collecting oximetry data relating to an oxygen saturation of the user, wherein the data relating to the parameter comprises the flow data and the oximetry data, and wherein the step of determining an amount of the collected data that is valid comprises determining an accumulated time during which the flow data and the oximetry data are simultaneously valid. Furthermore, the receiving, collecting, determining, storing, and providing steps may be performed using an apparatus having one or more sensors for collecting the data relating to the parameter, and wherein the receiving, collecting, determining, storing, and providing steps are repeated one or more times using the same apparatus.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various FIGS. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DESCRIPTION OF THE EXEMPLARY EMBODIMENTS

Figure 1:
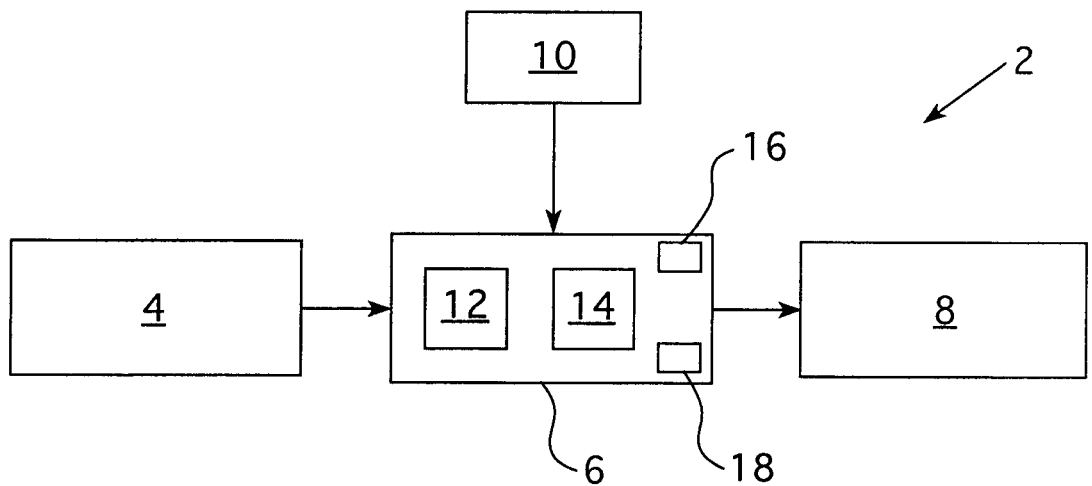
FIG. 1 is a schematic diagram of an apparatus for monitoring disordered breathing in accordance with the principles of the present invention.
Figure 2:
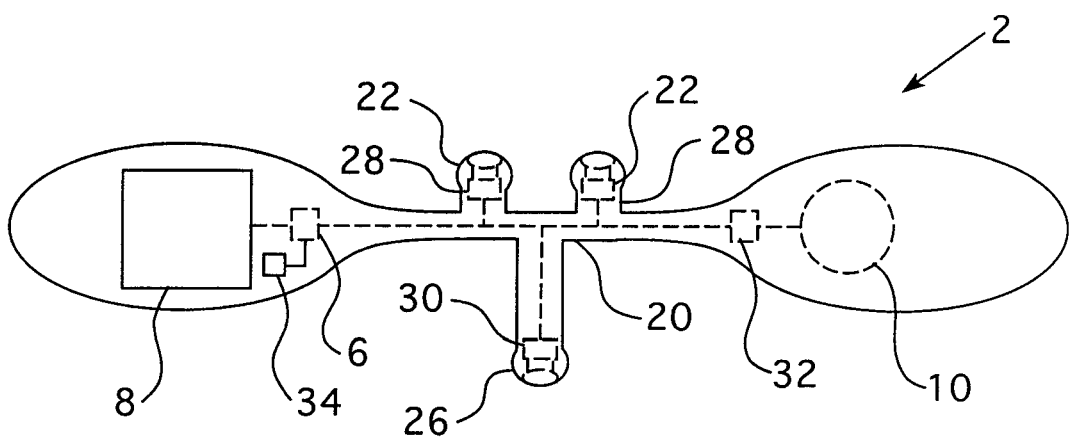
FIG. 2 illustrates an exemplary, non-limiting, first embodiment of a portable apparatus for monitoring disordered breathing in accordance with the principles of the present invention.
Figure 3:
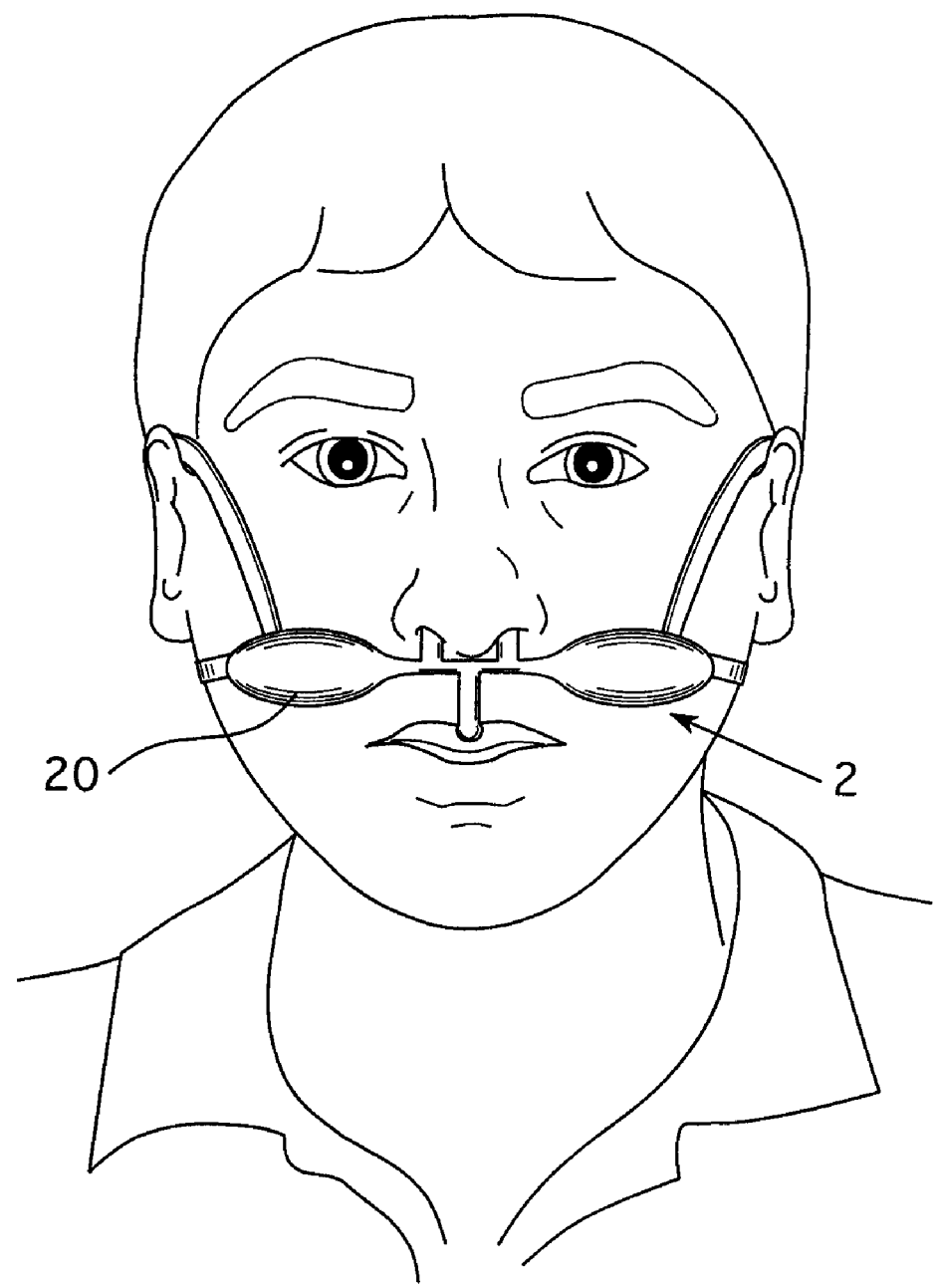
FIG. 3 is an illustration of the positioning of the apparatus of FIG. 2 on the face of a user.

FIGS. 1-3 illustrate an apparatus 2 for monitoring disordered breathing according to the principles of the present invention. In an exemplary embodiment, apparatus 2 is a portable apparatus adapted to be worn by the user. The present invention also contemplates that the monitoring techniques described herein can be used in a stationary monitoring system.

Apparatus 2 is particularly well suited for conducting a sleep study of a user, i.e., for studying the user during a sleep session, which typically lasts 4-10 hours. Apparatus 2 can be utilized when the user is sleeping to evaluate, for example, whether the user is experiencing sufficient events of disordered breathing to warrant that the user visit a medical professional for further evaluation. Events of disordered breathing that can be detected by apparatus 2 include, without limitation, apnea, hypopnea, mixed apnea/hypopnea, upper airway resistance syndrome, irregular breathing frequency, and/or Cheyne-Stokes respiration (CSR), snoring, hiccups, and coughing. Apnea is characterized by the cessation of airflow in the upper airway (oral and nasal) of the user for more than a predetermined interval of time, e.g., 10 seconds. Hypopnea is characterized by a reduction of airflow below a predetermined threshold level, e.g., one third to one half of normal airflow, for more than a predetermined interval of time, e.g., 10 seconds. Irregular breathing frequency is characterized by the user experiencing a number of breath cycles per unit of time exceeding or falling below a predetermined number of breath cycles per unit of time. For example, if a user's normal sleep breathing frequency is 12 breaths per minute, an exemplary irregular breathing frequency might be a breathing frequency of 24 breaths per minute.

Cheyne-Stokes respiration is characterized by alternating periods of apnea or shallow breathing and deep, rapid breathing. The cycle begins with slow, shallow breaths that gradually increase in depth and rate and is then followed by a period of apnea or shallow breathing. Each cycle can last 5 to 30 seconds. The cycle then repeats every 45 seconds to 3 minutes. CSR is well-known in the art and will not be described further herein for purpose of simplicity.

With reference to FIG. 1, apparatus 2 includes a flow sensor assembly 4 and a controller 6 for processing the output of flow sensor assembly 4. Controller 6 is connected to an output device 8, which is configured to output a user discernible indication related to or indicative of the results of a sleep study made by apparatus 2. The present invention contemplates that output device 8 can be implemented by a visual display such as an LED or LCD, an audio output device, such as a speaker, or a combination thereof. However, output device 8 is not to be construed as limited to a visual display and/or an audio output device.

Apparatus 2 can also include a self contained or remote power source 10 for providing power to flow sensor assembly 4, controller 6 and output device 8. Where apparatus 2 is portable, power source 10 can be a battery of suitable size, potential, and energy storage capacity.

With reference to FIG. 2 and with continuing reference to FIG. 1, a non-limiting physical embodiment of apparatus 2 includes a housing 20 defining a pair of nostril protrusions 22 and a mouth protrusion 26. Each nostril protrusion 22 houses or supports a flow sensor 28, while mouth protrusion 26 houses or supports a flow sensor 30. The present invention contemplates that flow sensors 28, 30 are any device capable of detecting a flow of gas and providing an output indicative thereof. Examples of suitable flow sensors include, a thermistor, a humidity sensor, a pressure transducer or any combination thereof. Flow sensors 28 and 30 are capable of detecting corresponding nostril or mouth airflow when housing 20 is properly positioned between the nose and the upper lip of the user. Flow sensors 28, 30 collectively define flow sensor assembly 4. However, this is not to be construed as limiting the invention since flow sensor assembly 4 can include more or less flow sensors.

Desirably, flow sensors 28, 30 are connected in series with controller 6. However, this is not to be construed as limiting the invention, because flow sensors 28, 30 can be connected to controller 6 in parallel or in some combination of series and parallel configurations.

In the illustrated exemplary embodiment, controller 6 includes an analog-to-digital converter (ADC) 12, a central processing unit (CPU) 14, memory 16 and an oscillator 18. Under the control of CPU 14, ADC 12 samples the analog signal(s) output by flow sensors 28, 30 in response to airflow into and out of one or more nostrils and/or the mouth of the user. In a manner known in the art, ADC 12 converts each sampled analog signal into a corresponding sample of digital data for storage in memory 16 and/or processing by CPU 14.

Oscillator 18 provides a clock signal for the operation of CPU 14 in a manner known in the art. Desirably, the frequency of oscillator 18 is such that CPU 14 can, among other things, determine a real-time duration of each event of disordered breathing as well as a time (TA) corresponding to the duration of the sleep study.

Housing 20 can include a component 32 for selectively electrically connecting controller 6 and output device 8 to power source 10. Component 32 can include a user activateable switch (not shown) that can be activated to electrically connect flow sensors assembly 4, controller 6, and output device 8 to power source 10 or deactivated to electrically isolate flow sensors assembly 4, controller 6, and output device 8 from power source 10. This enables the user to turn on or start the monitoring apparatus at the start of the sleep session and turn it off at the end, thereby conserving battery power.

With reference to FIG. 3 and with continuing reference to FIGS. 1 and 2, with housing 20 positioned between the nostrils and the mouth of the user, covering the user's philtrum, and upon activation of component 32 whereupon flow sensors assembly 4, controller 6, and output device 8 commence receiving electrical power from power source 10, CPU 14 commences sampling the signal(s) output by flow sensors 28, 30 prior to or at a time the user goes to sleep. The signals acquired during this pre-sleep period when the user is breathing normally enables apparatus 2 to establish baseline breath cycles of the user that CPU 14 can utilize to subsequently determine the occurrence of events of disordered breathing.

In order to enable the user to determine if apparatus 2 has established the necessary baseline breath cycles, CPU 14 can cause output device 8 to output a suitable user discernible audio and/or visual indication that CPU 14 has established the baseline breath cycles of the user.

Figure 4:
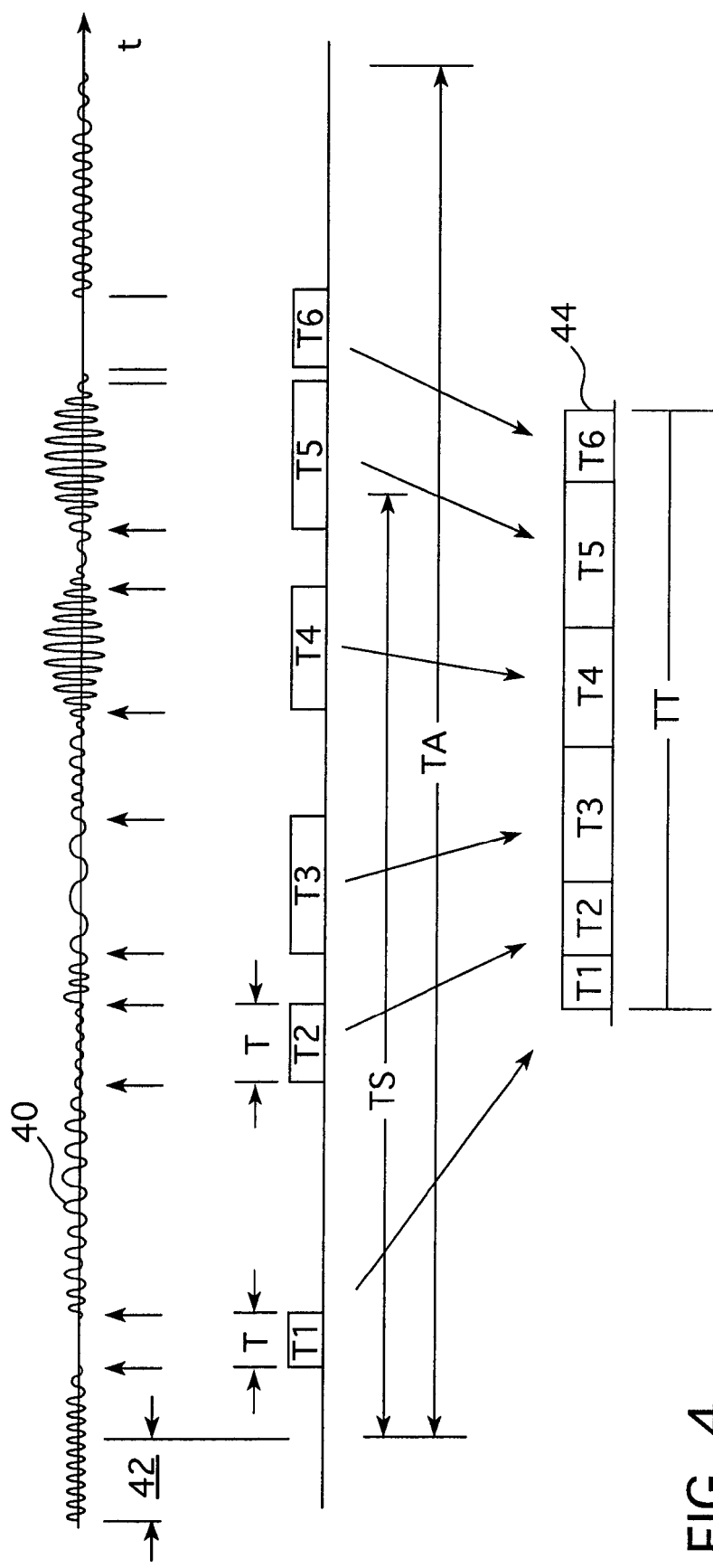
FIG. 4 is a chart illustrating the time intervals monitored by the monitoring device of present invention.

After output device 8 outputs the user discernible indication that the baseline breath cycles of the user has been established or after a suitable interval, such as 5-30 minutes, during which the user's normal breath cycles are being monitored by apparatus 2, the user typically goes to sleep. Thereafter, apparatus 2 monitors breath cycles of the user for disordered breathing events. As shown in FIG. 4, each time a disordered breathing event is identified, CPU 14 determines a time interval (T) over which the disordered breathing event occurs.

FIG. 4 illustrates a waveform 40 that corresponds to the flow of gas monitored by flow sensor assembly 4. A period of baseline breathing 42 is shown at the beginning of the sampled flow waveform. In this embodiment, a time interval T during which the patient experiences an apnea is identified as time interval T1. The length of time interval T1 corresponds to the length of the apnea, which must be at least 10 seconds to qualify as an apnea.

Examples of disordered breathing events include, without limitation, an apnea or hypopnea event lasting more than 10 seconds, a number of breaths per unit of time exceeding a predetermined number of breaths per unit of time, and/or a Cheyne-Stokes Respiration. Desirably, since a CSR often includes an apnea event, the time interval T of the disordered breathing event will be the time interval of the CSR event, not the time interval T of the apnea event associated with the CSR pattern. However, this is not to be construed as limiting the invention.

In FIG. 4, time interval T2 corresponds to a hypopnea, time interval T3 corresponds time interval during which the patient is experiencing variable breathing, e.g., breathing at a rate that is below (or above) a predetermined threshold, T4 corresponds to a first CSR event, time interval T5 corresponds to a second CSR event, and time interval T6 corresponds to another apnea. Again, the length of each time interval T1-T6 is determined based on the length of each disordered breathing event. The periods of time between each time interval are periods when no disordered breathing events are detected by apparatus 2. The duration of the entire monitoring session is indicated by time interval TA.

At a suitable time, CPU 14 causes output device 8 to output a user discernible indication that is a function of a total time (TT), which is related to or corresponds to a sum of the time interval(s) T. The summation of T1 through T6 in FIG. 4 to determine TT is shown by the collection of blocks 44. If the sleep study continues thereafter, CPU 14 can occasionally or periodically update output device 8 with a new user discernible indication that is a function of the current value of the total time TT about the time the update occurs. This occasional or periodic update can continue until the sleep study is complete.

An input device 34, such as a switch, can be provided to enable the user to signal to controller 6 the end of a sleep study. Also, or alternatively, apparatus 2 can be configured to terminate the sleep study, and, hence, the accumulation of time interval TA upon detecting the absence of signals output by airflow sensors 28, 30 for an extended period, as would occur when the user removes apparatus 2 from between his nostrils and mouth at the end of the sleep study.

Desirably, the detected disordered breathing events, and, hence, the time intervals T thereof, utilized as the basis for determining total time TT includes all of the detected disordered breathing events of the user. However, this is not to be construed as limiting the invention, because it is envisioned that the detected disordered breathing events utilized as the basis for determining total time TT can be less than all of the detected disordered breathing events of the user.

In the illustrated exemplary embodiment, time interval TA and each time interval T are determined by CPU 14 via the frequency of oscillator 18. Time interval TA is related to the duration controller 6 is conducting a sleep study. For example, time interval TA can be, without limitation, the entire duration of time commencing when controller 6 initially receives power from power source 10 to the time output device 8 outputs the corresponding user discernible indication; a time interval commencing 30 minutes after controller 6 initially receives power from power source 10 (i.e., the time the user goes to sleep) until the time output device 8 outputs the corresponding user discernible indication; a time interval that commences when controller 6 determines that the user has entered a sleep cycle until the time output device 8 outputs the corresponding user discernible indication; and the like. Controller 6 can determine when the user enters a sleep cycle with reference to the baseline breath cycles acquired before the user goes to sleep. Hereinafter, it will be assumed that time interval TA corresponds to the total time controller 6 is powered by power source 10 during a sleep study. However, this is not to be construed as limiting the invention since time interval TA can be selected by one of ordinary skill in the art to be any suitable time interval for purpose of conducting a sleep study.

Desirably, the user discernible indication is caused to be output by output device 8 after a minimum sleep study period TS, for example, four hours. To this end, controller 6 occasionally or periodically compares the current value of time interval TA to the minimum sleep study period TS and causes output device 8 to output the user discernible indication only after time interval TA is greater than the minimum sleep study period TS.

The user discernible indication output by output device 8 can include, without limitation, an indication of total time TT, an indication of which range of a plurality of predetermined ranges that total time TT falls into, and/or an indication whether a ratio of either TA/TT or TT/TA is greater than or less than a predetermined ratio.

For example, if apparatus 2 is operative during time interval TA for monitoring breath cycles for disordered breathing events and for determining for each disordered breathing event a time interval T over which the disordered breathing event occurs, the indication of the total time TT output by output device 8 can directly indicate the total time TT the user is experiencing disordered breathing during time interval TA. Also, or alternatively, controller 6 can include two or more ranges of total time that the total time TT can be compared to. The range within which total time TT falls into can then be output by output device 8. Also or alternatively, output device 8 can output an indication of whether the ratio TA/TT or TT/TA is greater than or less than a predetermined ratio. For example, the ratio TT/TA is essentially a ratio of the total time TT spent in disordered breathing events per time interval TA that can be compared to a predetermined ratio. Thus, if it is determined that the user is experiencing disordered breathing events in excess of 2.4 minutes per hour, i.e., >4% of the time the user is experiencing disordered breathing, output device 8 can be caused to output a corresponding usable discernible indication of this.

Also or alternatively, output device 8 can be caused to output a user discernible indication that the user should seek further medical evaluation if the user is experiencing disordered breathing events in excess of a predetermined number of minutes per hour or in excess of the predetermined percentage of the time. Also or alternatively, output device 8 can be caused to output a user discernible indication that the user need not seek further medical evaluation if controller 6 determines that the user is not experiencing disordered breathing events in excess of the predetermined number of minutes per hour or in excess of the predetermined percentage of the time.

In practice, the predetermined number of minutes per hour can be related to a percentage of total time TT spent in disordered breathing during a sleep study occurring over time interval TA, or vice versa. Obviously, the inverse of TT/TA, i.e., TA/TT, can also or alternatively be utilized as a basis for determining whether or not the user is experiencing excessive disordered breathing events and whether or not the user should seek further medical evaluation.

The choice of what information to output on output device 8 as a function of the total time TT described above is not to be construed as limiting the invention since it is envisioned that one of ordinary skill in the art can select the information to output on output device 8 as a function of the total time TT.

Controller 6 can operate any suitable manner to implement the present invention. For example, CPU 14 can record each sample of digital data acquired during a sleep study in memory 16 for occasional or periodic analysis by CPU 14 to determine if one or more sleep disordered breathing events have occurred. Alternatively, each sample of digital data can be stored in memory 16 in a moving window of sampled digital data corresponding to a predetermined analysis interval, e.g., a three minute moving window of time, that CPU 14 occasionally or periodically analyzes to determine if one or more sleep disordered breathing events have occurred. For each disordered breathing event determined to have occurred, CPU 14 can determine the corresponding time interval T over which the disordered breathing event occurred and can update total time TT with the time interval T, whereupon total time TT is a running tally of the sum of the time intervals T of all of the user's disordered breathing events detected by CPU 14. By way of oscillator 18, CPU 14 can keep a running tally of time interval TA.

Figure 5:
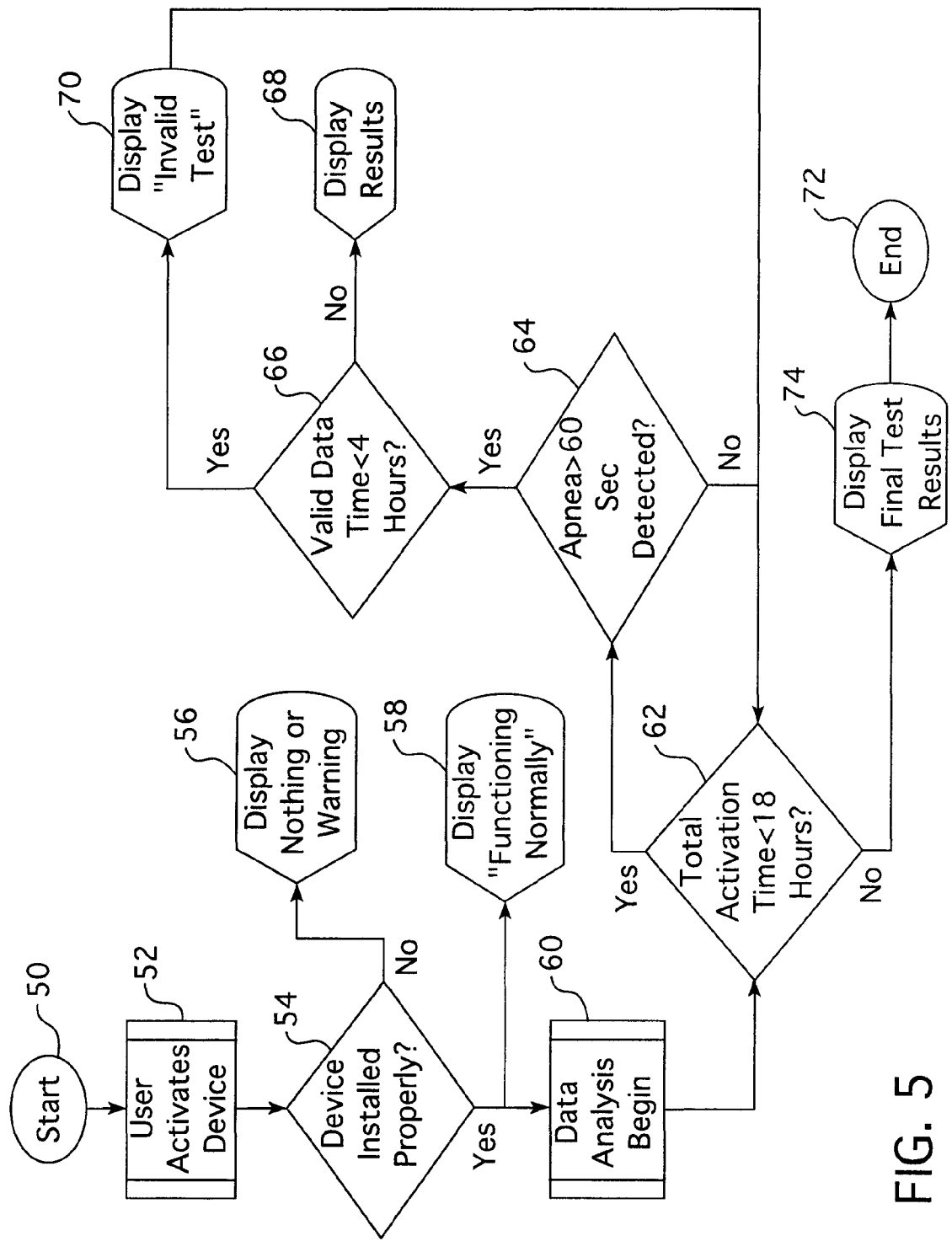
FIG. 5 is a flowchart illustrating an example of the operation of the monitoring device of present invention.

FIG. 5 illustrates the operation of the monitoring device of present invention according to one exemplary embodiment. As shown in FIG. 5, the monitoring process being in step 50 and proceeds to step 52 at which time the user activates apparatus 2. As noted above, activation of the monitor can be accomplished by means of component 32. In step 54 the apparatus performs a diagnosis to determine whether it is properly positioned on the user. This can be accomplished, for example, by monitoring the flow and comparing the detected flow to a template and/or by comparing a feature of the monitored flow, such as the frequency or peak, to predetermined thresholds. If the device is properly situated on the user, a certain fidelity of signal would be expected from the flow sensing assembly.

If the device is not properly mounted on the user, output device outputs a signal, such as an alarm, warning the user that the device is not properly positioned. See step 56. If the device is properly mounted on the user, the present invention contemplates providing an output on the output device that indicates that the device is functioning properly, such as a "functioning normally" message on the output device, as shown in step 58.

If the device is properly mounted on the user, it begins monitoring the flow of gas to and from the patient in step 60. As noted above, the present invention contemplates monitoring the patient during a baseline breathing period 42 so that the data, waveforms, breath information, etc. can be used for comparing to later signals.

In step 62 the system determines whether it has been operating, i.e., activated for less than 18 hours. The purpose of this step is to cause the device to shut down, stop collecting data, and display a final result after it has been operating for 18 hours. It can be appreciated that a time period other than 18 hours can be used in step 62. If the device has been operating for less than 18 hours, the process proceeds to step 64.

In step 64, the system checks whether an apnea lasting more than 60 seconds has been detected. A normal human will not have an apnea lasting this long. Thus, if a 60 second apnea is detected, it likely means that the apparatus has been removed from the patient. If no apnea longer than 60 seconds is detected, the system returns to step 62 and continues to monitor the patient until the system is deactivated or the time limit set forth in step 62 expires. It can be appreciated that the 60 second time period in step 64 can be set to other time periods.

As noted above, if a 60 second apnea is detected in step 64, it is presumed that the patient has taken off the monitoring device, and the process proceeds to step 66. In step 66, the system determines whether enough valid data has been collected during the time the system was being used in order to render a valid test result. In step 66, the system checks whether 4 hours worth of valid data has been collected. It can be appreciated that time periods other than 4 hours can be used in step 66. Valid data time means that the system is deemed to be accurately collecting data.

If 4 hours of valid data has been collected, i.e., if the total time of the valid data is not less then 4 hours, the system advances to step 68 and displays the result of the monitoring. In an exemplary embodiment of the present invention, the system compares the total time TT to a threshold level. If the total time TT exceeds the threshold, the patient is advised to consult his or her doctor. For example, a message, "See your Doctor" is displayed on output device 8. It is expected that the doctor will have the necessary tests preformed on the user to determine the type and severity of the breathing disorders, to determine an appropriate treatment. If the total time TT exceeds the threshold, the user is advised that the monitoring session does not indicate the need to consult a doctor. For example, a message "You're OK" can be displayed on output device 8.

If 4 hours of valid data has not been collected, i.e., if the total time of the valid data is less then 4 hours, the system advances to step 70. In step 70, the system displays a message indicating that the monitoring session failed to produce a valid result. For example, a message, "Invalid Test" is on output device 8. After steps 68 and 70, the system returns to step 62. By returning to step 62, the present invention contemplates that the user may put the apparatus back on so that it can continue to collect data. In an alternative embodiment, the stem proceeds to end step 72 and terminates the monitoring session.

If the system has been activated for 18 hours in step 62, it proceeds to step 74 and displays the final result of the monitoring session, such as "See your Doctor," "You're OK", or "Invalid Test". After step 74, the system continues to step 72 and terminates the monitoring session.

As can be seen, the present invention can determine events of disordered breathing of the user and, for each event, can determine a time interval T over which the event occurs. The total time TT related to the sum of the intervals T of all of the events of disordered breathing can also be determined and a user discernible indication related to or as a function of total time TT can be output. The indication that is output can be the total time TT; an indication of which of a number of predetermined ranges total time TT falls into; or an indication whether a ratio of either TA/TT or TT/TA is greater than or less than a predetermined ratio. Also or alternatively, the user discernible indication can include an indication whether or not the user should seek further medical evaluation. Desirably, time interval TA is no less than a minimum acceptable time interval TS for conducting a sleep study.

Use of total time TT as a basis for evaluating whether or not a user has a sleeping or breathing disorder enables a broader range of disordered breathing events to be utilized as a basis for determining whether or not the user needs to seek further medical evaluation regarding a sleeping or breathing disorder. This is in contrast to the prior art, which only determines the occurrence of apnea events and outputs an indication of the number of events thereof or a diagnosis related thereto.

Also or alternatively, apparatus 2 can be configured to detect and record a user snoring. In this configuration of apparatus 2, at least flow sensor 30 is desirably a pressure transducer, e.g., a piezoelectric transducer, that can detect the sound of a user snoring.

In use of this configuration of apparatus 2, ADC 12, under the control of CPU 16, samples the analog signal(s) output by flow sensor 30 in the form of a pressure transducer in response to the user snoring. ADC 12 converts each sampled analog signal into a corresponding sample of digital data for storage in memory 16 and/or processing by CPU 14.

Each time CPU 14 detects a user snoring event, which can be accomplished using any snore detecting technique, CPU 16 determines a time interval S of the snoring event in a manner know in the art via the frequency of oscillator 18. At a suitable time, CPU 16 also determines a total time SS which is related to a sum of the time interval(s) S of a subset of the snoring events of the user. The subset of snoring events can include all of the detected snoring events or less than all of the detected snoring events. Examples of systems that are capable of detecting snoring are described in U.S. Pat. Nos. 5,203,343; 5,458,137; 6,085,747, and 7,246,619.

Controller 6 can operate in any suitable manner to detect snoring events. For example, in the manner similar to that described above, CPU 14 can record each sample of digital data acquired during a sleep study in memory 16 for occasional or periodic analysis by CPU 14 to determine if a snoring event has occurred. Alternatively, each sample of digital data can be stored in memory 16 in a moving window of sampled digital data corresponding to a predetermined analysis interval, e.g., a three minute moving window of time, that CPU 14 occasionally or periodically analyzes to determine if one or more snoring events have occurred. For each snoring event determined to have occurred, CPU 14 can determine the corresponding time interval S over which the snoring event occurred and can update total time SS with the time interval S, whereupon total time SS is a running tally of the sum of the time intervals S of all of the user's snoring events detected by CPU 14.

In an exemplary non-limiting embodiment, a snoring event comprises airflow sensor 30 in the form of a pressure transducer outputting to ADC 12 an analog signal having an amplitude greater than a predetermined threshold level for longer than a predetermined period of time, e.g., $\geq 1$ sec.

Because snoring is related to inhalation and since the disordered breathing events described above are related to exhalation, sensor 30 in the form of a pressure transducer can be utilized for detecting both disordered breathing events and snoring events. However, this is not to be construed as limiting the invention since it is envisioned that sensor 30 can comprise two separate detection elements (not shown), one of which is a pressure sensor for detecting snoring events and the other of which is a thermistor or humidity sensor for detecting disordered breathing events.

In the manner similar to that described above, output device 8 can also be caused to output a user discernable indication related to, without limitation, an indication of total time SS, an indication of which range of a plurality of predetermined ranges that total time SS falls into, and/or an indication whether a ratio of either TA/SS or SS/TA is greater than or less than a predetermined ratio.

As can be seen, the present invention can also determine snoring events of the user and, for each such event, can determine a time interval S over which the event occurs. The total time SS related to the sum of the intervals S of all of the snoring events can also be determined and a user discernible indication related to or as a function of total time SS can be output. The indication that is output can be the total time SS; an indication of which of a number of predetermined ranges total time SS falls into; or an indication whether a ratio of either TA/SS or SS/TA is greater than or less than a predetermined ratio. Also or alternatively, the user discernible indication can include an indication whether or not the user should seek further medical evaluation for a possible snoring disorder.

Figure 6:
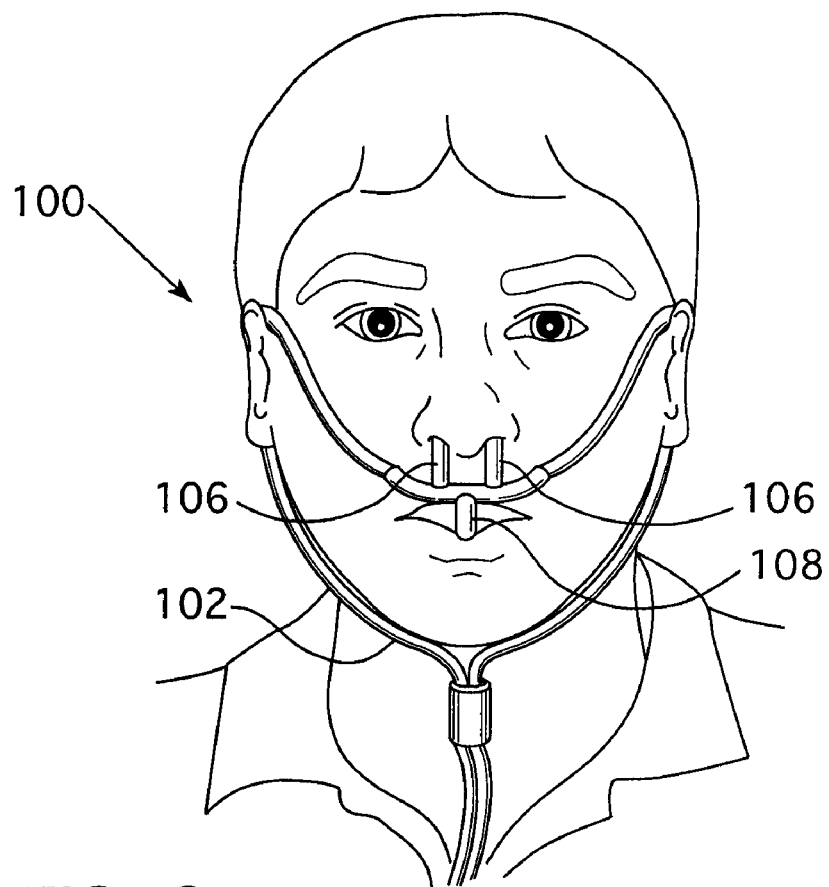
FIGS. 6 and 7 illustrate an exemplary, non-limiting, second embodiment of a portable apparatus for monitoring disordered.
Figure 7:
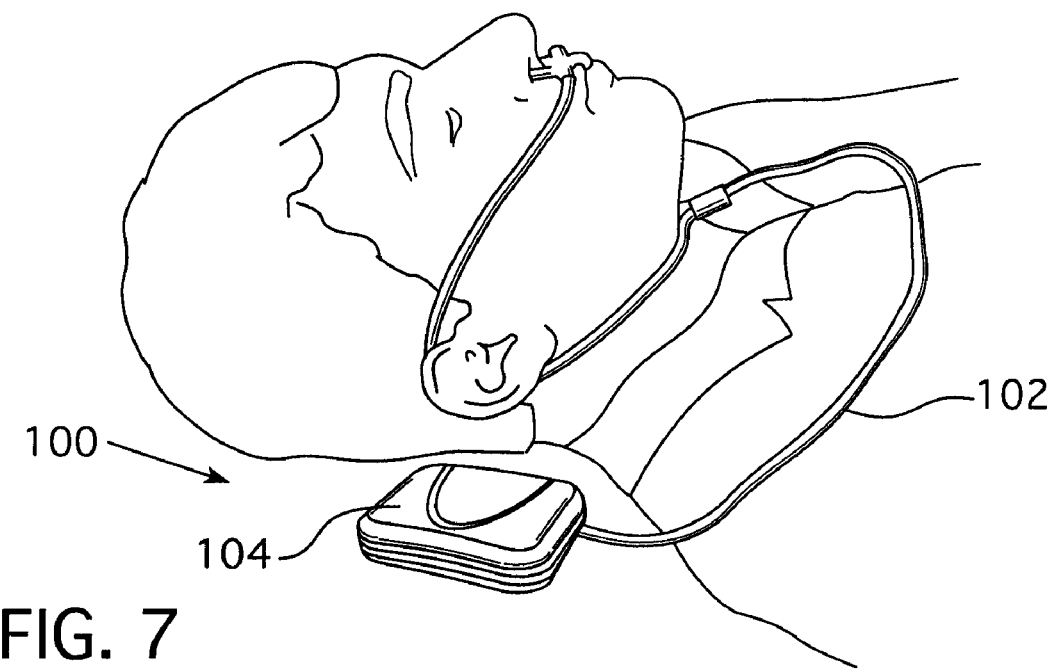

FIGS. 6 and 7 illustrate an exemplary, non-limiting, second embodiment of a portable apparatus 100 for monitoring disordered breathing in accordance with the principles of the present invention. Instead of housing the entire system on the head of the user, as with the embodiment of FIG. 3, apparatus 100 is devised of two basic parts: a part that monitors the user, such as a cannula 102, and a separate housing 104. Cannula 102 is essentially a hollow tube that is in fluid communication with the nasal and oral passages of the user. A pair of prongs 106 are disposed proximate to the nares to monitor nasal respiration and a single prong 108 is disposed proximate to the mouth to monitor oral respiration. Cannula can be a single lumen cannula or a multi-lumen cannula.

One or more sensors, such as flow sensors, temperature sensors, or pressure sensors, are disposed in hosing 104. The output from the sensor is used by a processor in the housing to determine when the patient is experiencing disordered breathing and to accumulate the amount of time during which disordered breathing occurs, as discussed above. The results of the monitoring session can be displayed in housing 104 using any conventional format, such as LED or a display.

It can be appreciated that the present invention provides a device and method for detecting a range of sleep disordered breathing that is much greater than conventional devices and methods that detect only snoring or apneas. It be further appreciated that the present invention provides a device and method for analyzing and displaying the results of a sleep study for disordered breathing events and/or snoring events that utilizes a common metric for reporting whether or not the user is experiencing such events, regardless of their type.

Figure 8:
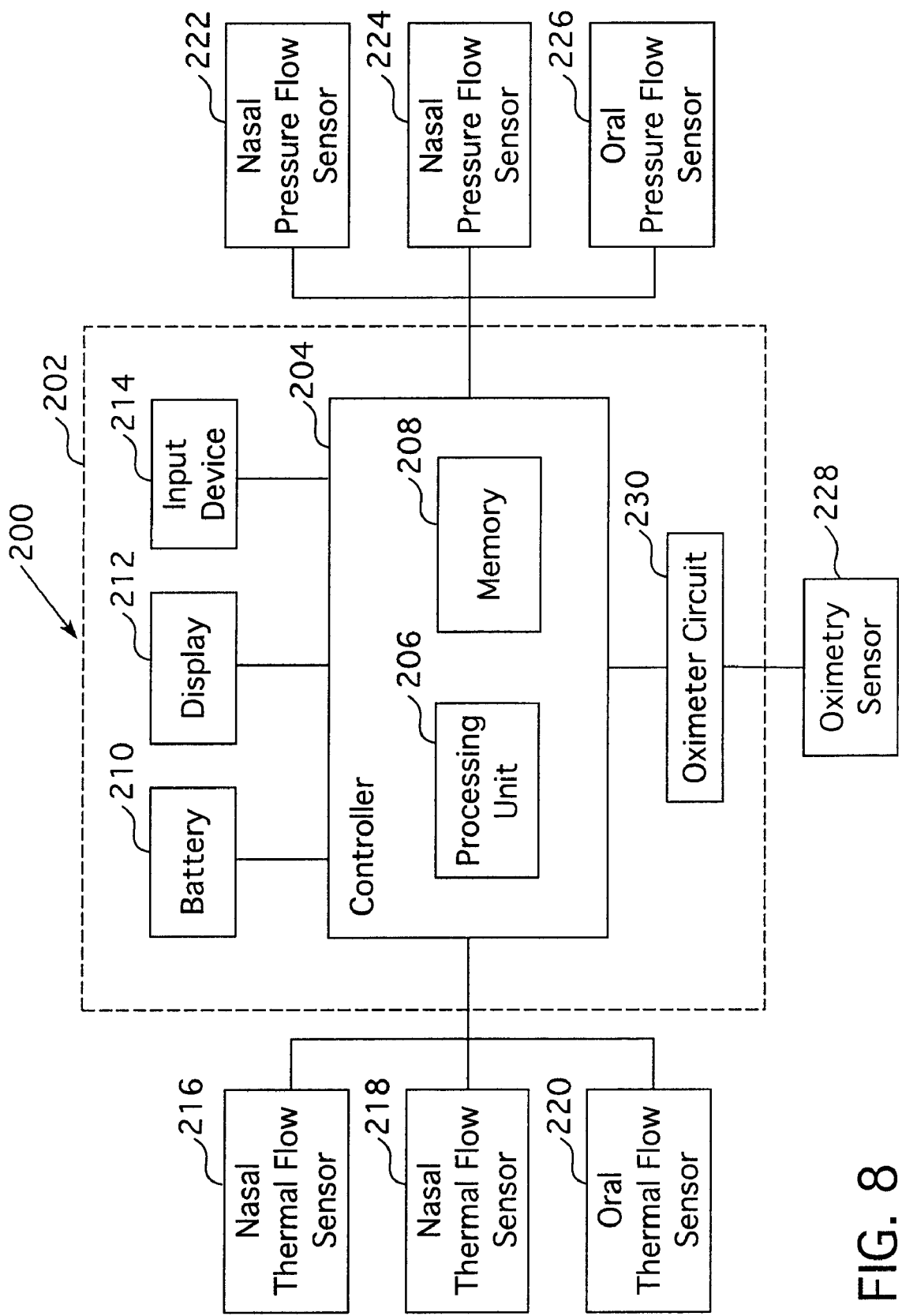
FIG. 8 is a block diagram of a data recorder according to a further non-limiting embodiment of the invention.

FIG. 8 is a block diagram of a data recorder 200 according to a further non-limiting embodiment of the invention. As described in more detail below, data recorder 200 is adapted to collect various sleep-related parameters from the patient and provide a status indicator to the patient which indicates the amount of valid sleep study data that has been collected by the data recorder, preferably as compared to some predetermined amount of valid data that is required in order to deem the study valid. Thus, a patient will be able to determine whether or not a sufficient amount of valid data has been recorded prior to returning data recorder 200 to the clinician supervising the sleep study. As a result, if insufficient data has been collected during one particular sleep period (i.e., one overnight period), the study can be repeated at another time, for example the next night. In addition, an indication that insufficient valid data has been collected may be used as a signal to the patient that the patient may not be properly using data recorder 200 (for example, the patient may not be properly positioning one or more of the sensors described herein).

Portable data recorder 200 includes a housing 202 which includes a controller 204. As seen in FIG. 8, controller 204 preferably includes a processing unit 206 and a memory 208. In one particular non-limiting embodiment, controller 204 is an application specific integrated circuit (ASIC) that includes a microcontroller or some other similar suitable processor and internal memory, such as, without limitation, an internal EEPROM and/or flash memory. Alternatively, controller 204 may include discrete elements, wherein processing unit 206 is, for example, a microprocessor, a microcontroller, or some other suitable processor and memory 208 is an EEPROM and/or flash memory that is external to the processing unit. As still a further alternative, controller 204 may simply comprise processing unit 206 having an internal memory. In addition, data recorder 200 includes a battery 210 or some other suitable power source for providing power to the data recorder, a display 212, such as, without limitation, a liquid crystal display (LCD) for displaying information related to the operation of the data recorder as described elsewhere herein, and an input device 214 for inputting information and/or commands into the data recorder such as, without limitation, the configuration information described elsewhere herein.

As seen in FIG. 8, data recorder 200 further includes a plurality of flow sensors that are operatively coupled to controller 204 through housing 202. In particular, in the non-limiting embodiment shown in FIG. 8, data recorder 200 includes nasal thermal flow sensors 216 and 218, which are structured to be received within the nostrils of the patient and oral thermal flow sensor 220, which is structured to be positioned adjacent to the patient's mouth. Nasal thermal flow sensors 216 and 218 and oral thermal flow sensor 220 are structured to detect nostril and mouth gas flow, respectively, when the patient breaths in and out based on temperature changes as sensed by flow sensors 216, 218 and 220.

In an exemplary embodiment, thermal flow sensors 216, 218 and 220 each include a thermistor or some other suitable temperature sensing device for this purpose. It should be noted that the embodiment shown in FIG. 8 is meant to be exemplary, and that different temperature based flow sensor configurations are possible within the scope of the claimed invention. For example, only nasal thermal flow sensor 216 and/or nasal thermal flow sensor 218 may be provided for detecting temperature based flow data, or, alternatively, only oral thermal flow sensor 220 may be provided for detecting temperature based flow data.

In addition, data recorder 200 in the non-limiting embodiment shown in FIG. 8 further includes nasal pressure flow sensors 222 and 224, which are structured to be received within the nostrils of the patient, and an oral pressure flow sensor 226, which is structured to be positioned adjacent to the patient's mouth. Nasal pressure flow sensor 222, nasal pressure flow sensor 224, and oral pressure flow sensor 226 are also provided for collecting flow data relating to the flow of gas inhaled and exhaled by the patient and are adapted to do so based upon pressure that is sensed by each of nasal pressure flow sensor 222, nasal pressure flow sensor 224, and oral pressure flow sensor 226. For this purpose, each of nasal pressure flow sensor 222, nasal pressure flow sensor 224, and oral pressure flow sensor 226 include a pressure transducer.

It should be noted that the embodiment shown in FIG. 8 is meant to be exemplary, and that different pressure based flow sensor configurations are possible within the scope of the claimed invention. For example, only nasal pressure flow sensor 222 and/or nasal pressure flow sensor 224 may be provided for detecting pressure based flow data, or, alternatively, only oral pressure flow sensor 226 may be provided for detecting temperature based flow data.

Thus, the embodiment of data recorder 200 shown in FIG. 8 is structured to collect flow data relating to the flow of gas inhaled and exhaled by the patient in two ways, namely based on temperature and based on pressure. While this is the preferred embodiment shown in FIG. 8, it is to be understood that this is not meant to be limiting, and that flow data may be collected by only one of the methods (i.e., only thermally and/or only using pressure). In addition, it is to be understood that other suitable methods of collecting flow data are possible. For example, the flow data could come from a separate pressure based therapy device such as a CPAP machine where data recorder 200 would receive and analyze the flow signal provided by the therapy device.

Preferably, flow sensors 216 through 226 are applied to the patient using an assembly that is similar to an oxygen cannula, which is applied in the nostrils with continuation over the patient's ears and secured under the patient's chin in a manner that flow sensors 216 through 226 are positioned properly.

Data recorder 200 further includes an oximetry sensor 228 for collecting data relating to the oxygen saturation of the blood of the patient. Such oximetry sensors 228 are well known and are typically structured to placed on the patient's body, typically on the patient's finger (although this is preferred, it is not limiting and other body parts are possible for a placement of the sensor device). Oximetry sensor 228 typically includes two key elements, namely an emitter which outputs multiple wavelengths of red and infrared light, and a detector. The elements are positioned within the oximetry sensor so that they are positioned on opposite sides of the patient's finger. The oximetry sensor is operatively coupled to an oximeter circuit 230 provided within housing 202. Oximeter circuit 230 receives the data collected by oximetry sensor 228 and, using known algorithmic analysis methods, determines an oxygen saturation level of the patient, which data is provided to controller 204. Alternatively, oximeter circuit 230 may be external to housing 202 (for example, in its own housing) with a suitable connection being made between oximeter circuit 230 and controller 204 through housing 202.

It is to be further understood that the present invention further contemplates that the communications between sensors 216-228 and controller 204 can be a wireless or a hardwired communication link. Similarly, the communications between oximeter circuit 330 and controller 204 can be a wireless or a hardwired communication link. Moreover, data recorder 200 can include further input/output devices for providing information to or receiving information from a remote locations. Examples, of such input/output devices include modems, RS-232 ports, serial ports, USB ports, a Bluetooth communication link, etc.

According to an aspect of the invention, data recorder 200 provides a visual status indicator that indicates the status of the study being conducted. In particular, the status indicator preferably provides a visual indication of how much valid data has been collected as compared to a predetermined required amount of valid data that is set by, for example, a clinician. FIGS. 9A-9D show one exemplary embodiment of data recorder 200 having a status indicator 235 provided on display 212 in the form of a pie chart. The pie chart in this embodiment, has four separate sections, with the number of sections that are darkened indicating the percentage of completion of the sleep study (resolved to 25% increments).

Figure 9A:
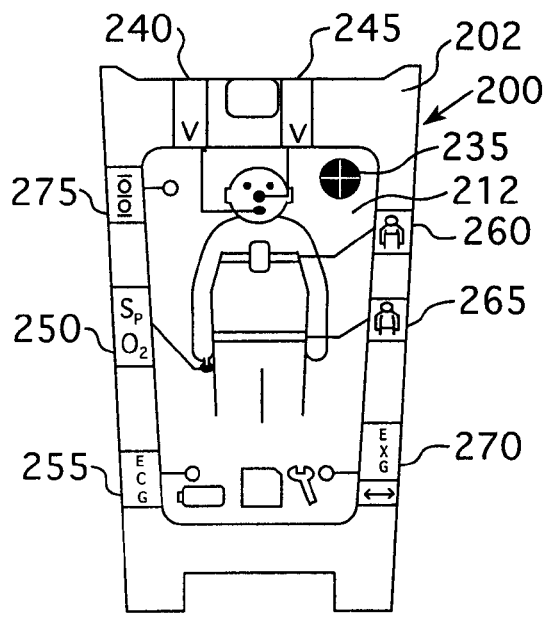
FIGS. 9A-9D show one exemplary embodiment of the data recorder wherein a status indicator provided thereon is in the form of a pie chart.

In status indicator 235 shown in FIG. 9A, all four of the sections have been darkened, which indicates that the sleep study has been completed with sufficient valid data as compared to the predetermined required amount of valid data (i.e., 100% or more valid data as compared to the required valid data). Status indicators 235 in FIGS. 9B, 9C, and 9D indicate 25% completion, 50% completion, and 75% completion, respectively, by having the appropriate number of sections darkened therein. In other words, the status indicators in FIGS. 9A-9D indicate that 100%, 25%, 50%, and 75%, respectively, of the required valid data has been collected by data recorder 200. Thus, the patient will be able to determine from status indicator 235 whether they should return data recorder 200 to the clinician so that the data can be analyzed, or whether the sleep study should be repeated.

It is expected that the clinician or other healthcare provider, when instructing the patient in the use of data recorder 200, will explain the purpose of status indicator 235 and will tell the patient that they will call the patient in the morning after a sleep study has been conducted to inquire how the study went (i.e., the nature of status indicator 235). If the patient reports insufficient data as reported by status indicator 235, the clinician can counsel the patient on the proper use of data recorder 200 (e.g., the proper placement and use of the sensors) and how they may improve the application on the next study.

The present invention contemplates that the visual status indicator described herein is specific to each night or session of recorded data since, in an exemplary embodiment, the valid data must be collected in a single recording session and not the composite of multiple nights of recording. The present invention further contemplates storing one or more prior visual status indicators by data recorder 200 so that the data recorder can provide an ability for the patient to recheck the last visual status indicator in the event that they shut off the data recorder without checking it. However, as noted above, the present invention contemplates resetting the visual status indicator on each subsequent recording after a short period of recording time has elapsed.

Also referring to FIGS. 9A-9D, the embodiment of data recorder 200 shown therein includes a housing 202 having a number of ports for making connections to the housing, and, in particular, to controller 204 housed therein. Specifically, a port 240 is provided for allowing thermal flow sensors 216-220 to be operatively coupled to the housing. A port 245 is provided to allow pressure flow sensors 222-226 to be operatively coupled to housing 202. A port 250 is provided for enabling oximetry sensor 228 to be operatively coupled to housing 202, and, in particular, to the oximeter circuit 230 and the controller 204.

Figure 9B:
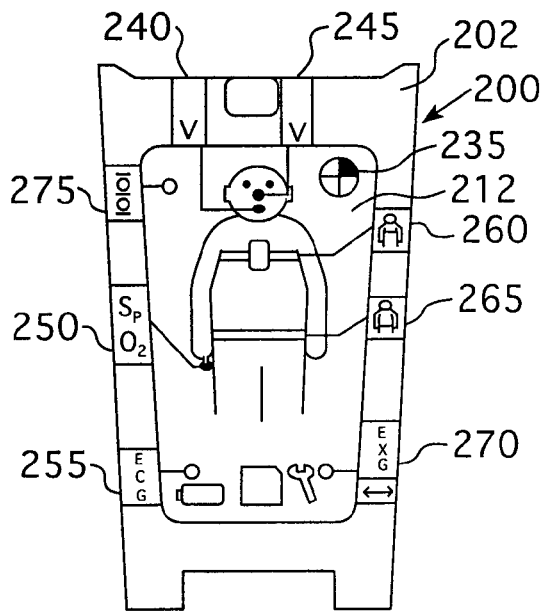
Figure 9C:
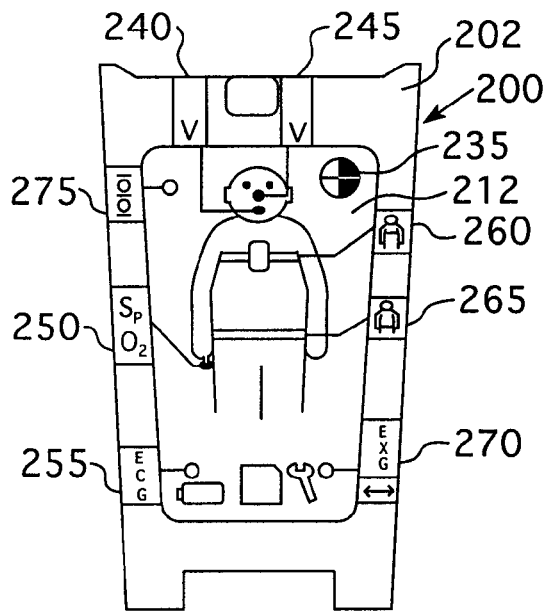
Figure 9D:
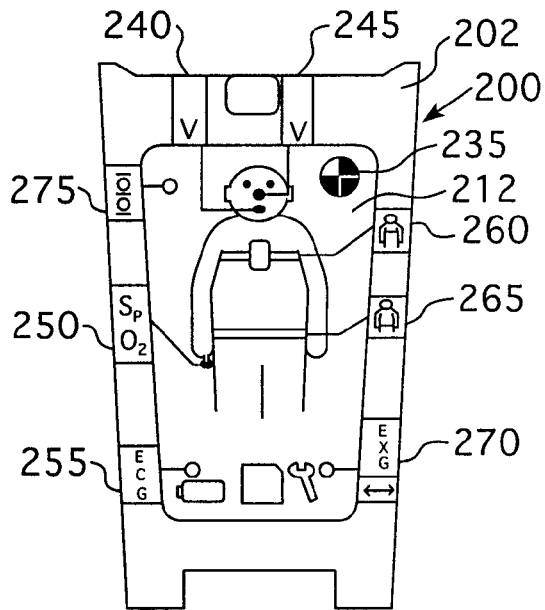

In the exemplary embodiment shown in FIGS. 9A-9B, housing 202 also includes a port 255 for enabling an ECG sensor to be operatively coupled to the housing, a port 260 for allowing a thoracic plethysmography device to be operatively coupled to the housing and controller 204, a port 265 for allowing an abdominal plethysmography device to be operatively coupled to the housing and the controller, and a port 270 for allowing an ExG device or an actigraphy device to be operatively coupled to the housing and the controller. Furthermore, an I/O port 275 is provided to enable data recorder 200 to be electronically connected to another device such as a PC so that data can be input into data recorder 200 or output from the data recorder 200. I/O port 275 may also be used to connect to and collect additional data from a separate therapy device such as a CPAP machine.

It is to be understood that the particular embodiment of data recorder 200 shown in FIGS. 9A-9D, and, in particular, the embodiment of status indicator 235 shown therein, is meant to be exemplary only, and that other embodiments may be provided within the scope of the claimed invention. For example, and without limitation, status indicator 235 could be percentage value (e.g., "100%" or "50%") that is displayed on display 212 based upon the valid data that is collected as compared to the required amount of valid data. In addition, different numbers of sections (i.e., different percentage increments) and/or different shapes (e.g., a square shape) may be used for status indicator 235. Other variations are also possible.

Figure 10:
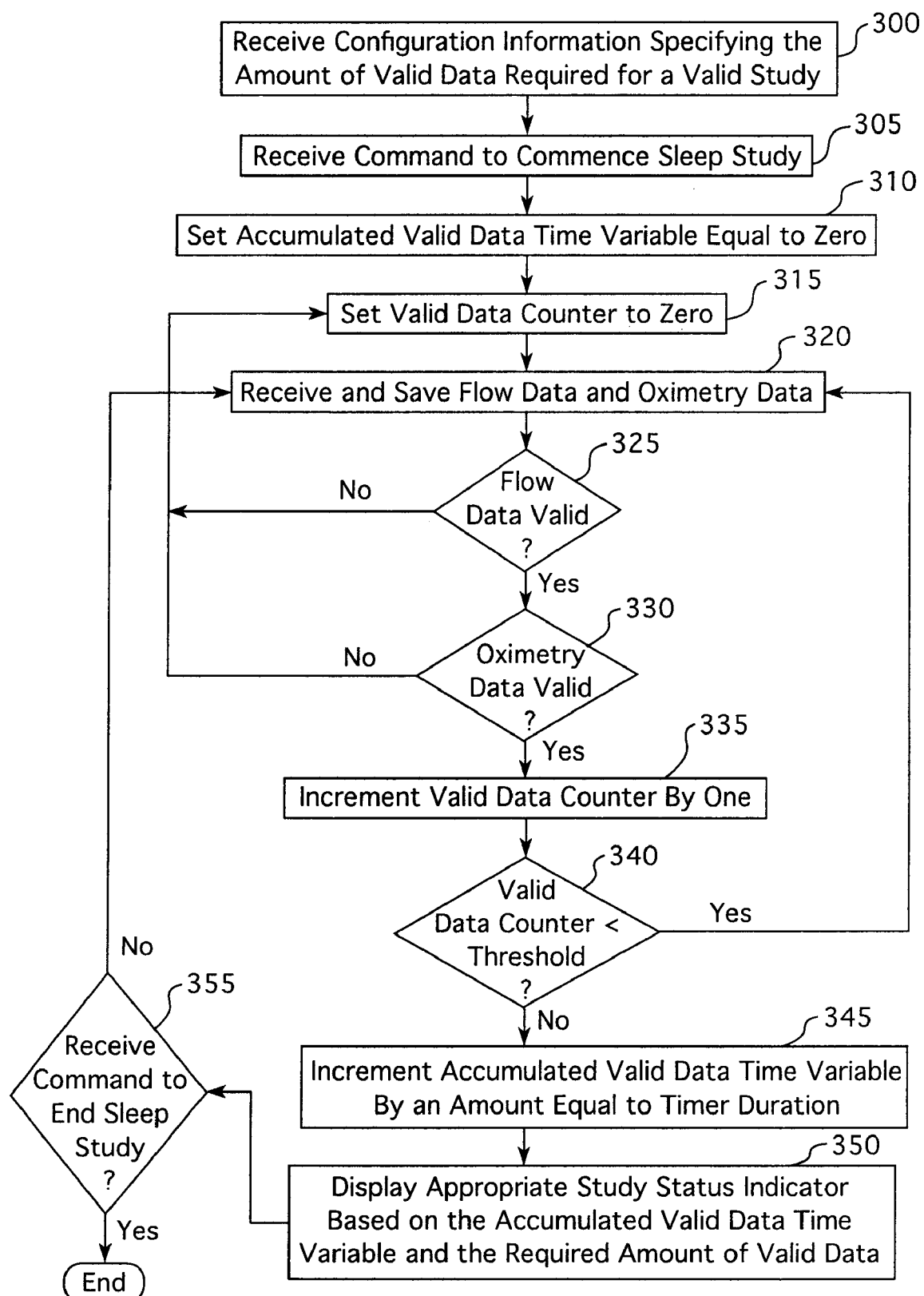
FIG. 10 is a flowchart showing a method of collecting data and providing a status indicator indicating the amount of valid data that has been collected according to one particular embodiment of the present invention.

FIG. 10 is a flowchart showing a method of collecting data and providing a status indicator indicating the amount of valid data that has been collected according to one particular embodiment of the present invention. As will be appreciated, the method shown in FIG. 10 may be implemented in one or more routines stored in memory 208 and executable by processing unit 206 shown in FIG. 8. In addition, as described below, in the particular embodiment shown in FIG. 10, the method is configured such that both flow data and oximetry data are collected and both must be determined to be valid for the data to be considered good. It will be appreciated, however, that the method may alternatively be configured such that only one of flow data and oximetry data is collected and such that only that data needs to be valid to be considered good.

The method begins at step 300, wherein controller 204 receives configuration information which specifies the amount of valid data required for a study to be deemed valid. For example, a clinician may specify that at least eight hours of valid data is required in order for a particular sleep study to be deemed valid. The configuration information may be entered using input device 214 shown in FIG. 8, which may comprise one or more buttons provided on housing 202 and/or may comprise a touch screen forming part of display 212, or from an external device such as a clinician's PC using the I/O port 275. Next, at step 305, controller 204 receives a command to commence a sleep study. Specifically, the patient may enter such a command using input device 214 after the sensors shown in FIG. 8 have been attached as required and the patient is ready to go to sleep.

Next, at step 310, an accumulated valid data time variable is set equal to zero. As will be described below, this variable is used to track the cumulative amount of valid data (in terms of time) that has been collected during the sleep study as determined by the data recorder 200. Then, at step 315, a valid data counter is set to zero. In the preferred embodiment, as described below, in order for data to be considered to be valid, flow data and oximetry data must be simultaneously valid for a predetermined period of time, such as, without limitation, one minute. As described in greater detail below, the valid data counter is used to measure the passage of time. In particular, the valid data counter is incremented each time simultaneous samples of valid data are obtained. Thus, as will be appreciated, when a certain counter threshold value (based on the chosen data sampling rate and the chosen predetermined period of time described above) is reached, that will indicate that the predetermined period of time has elapsed. For example, with a data sampling rate of 100 ms, a valid data counter value of 600 will indicate that one minute has passed.

At step 320, controller 204 receives flow data relating to gas that is breathed in and out by the patient and oximetry data that relates to the oxygen saturation of the patient. In the preferred embodiment, the data is received (sampled) every 100 ms, although other sampling rates may also be used. Also in the preferred embodiment, the flow data is collected using both thermal flow sensors 216-220 and pressure flow sensors 222-226 shown in FIG. 8. The oximetry data is collected using oximeter sensor 228 and oximeter circuit 230 shown in FIG. 8. Next, at step 325, a determination is made as to whether the flow data that was collected (i.e., the current sample) is valid. The purpose of this check is to detect evidence of breathing.

Determining whether the flow data that was collected is valid may be done in a number of different ways. For example, in one embodiment, the flow data may be used to generate flow waveforms, and the data will be considered to be valid based on the peak-to-peak changes in the waveforms, and, in particular, if such changes are greater than some empirically determined noise threshold value. The particular noise threshold value is preferably determined during testing of the particular implementation of the data recorder 200 that is employed. One particular non-limiting implementation for determining whether flow data is valid in this manner is described elsewhere herein. In addition, in one embodiment, the flow data will be considered to be valid if either the data from thermal flow sensors 216-220 is determined to be valid or the data from pressure flow sensors 222-226 is determined to be valid as described herein. Alternatively, in another embodiment, the flow data will be considered to be valid only if both the data from thermal flow sensors 216-220 and the data from pressure flow sensors 222-226 is determined to be valid as described herein.

Referring again to FIG. 10, if the answer at step 325 is no, meaning the flow data is not valid, then the method returns to step 315, and the valid data counter is reset to zero. If, however, the answer at step 325 is yes, then, at step 330, a determination is made as to whether the oximetry data (i.e., the current sample) is valid. This may also be done in a number of ways. In one particular non-limiting embodiment, the oximeter circuit 230 will output (each time it is sampled) an oxygen saturation data value and status byte information. The oxygen saturation data value will be set to zero if an error indicating invalid oxygen saturation data is detected by oximeter circuit 230 (otherwise an actual data value greater than zero is output). In addition, the status byte information that is output will be considered to be valid if (i) it has the proper format (i.e., most-significant bit equal to one), and (ii) all error status bits are equal to zero. For the oximetry data to be deemed valid in this particularly embodiment, the oxygen saturation data value must be greater than zero and the status byte information must be valid.

If the answer at step 330 is no, meaning that the oximetry data is not valid, then the method returns to step 315 and the valid data counter is reset to zero. If, however, the answer at step 330 is yes, meaning that both the flow data and the oximetry data are valid, then, at step 335, the valid data counter is incremented by one. Next, at step 340, a determination is made as to whether the valid data counter is less than some predetermined threshold value that, as discussed elsewhere herein, is chosen based on the data sampling rate and the predetermined time for which flow and oximetry data must be simultaneously valid. In the preferred embodiment, the data sampling rate is 100 ms, the predetermined time for which flow and oximetry data must be simultaneously valid is one minute, and the threshold value is 600. It is to be understood that other values for these parameters are also possible.

If the answer at step 340 is yes, then the method returns to step 320 wherein the next flow data and oximetry data samples are received. If, however, the answer at step 340 is no, then that means that valid flow data and valid oximetry data have been simultaneously received for the predetermined duration (e.g., one minute), and therefore, the method will proceed to step 345. At step 345, the accumulated valid data time variable is incremented by an amount equal to the predetermined time for which flow and oximetry data must be simultaneously valid (e.g., one minute). This is done because it has been determined in the prior steps than an amount of valid data equal to that predetermined time has been collected.

Next, at step 350, an appropriate study status indicator based on the accumulated valid data time variable and the required amount of valid data is displayed on display 212. In the preferred embodiment, the study status indicator has the form of status indicator 235 shown in FIGS. 2A through 2D. Following step 350, the method proceeds to step 355, wherein a determination is made as to whether a command to end the sleep study has been received by the controller 204 by for example, receiving an input from the patient through the input device 214 at the end of the night. If the answer is no, then the method returns to step 320, wherein data collection continues. If the answer at step 355 is yes, the method ends.

Figure 11:
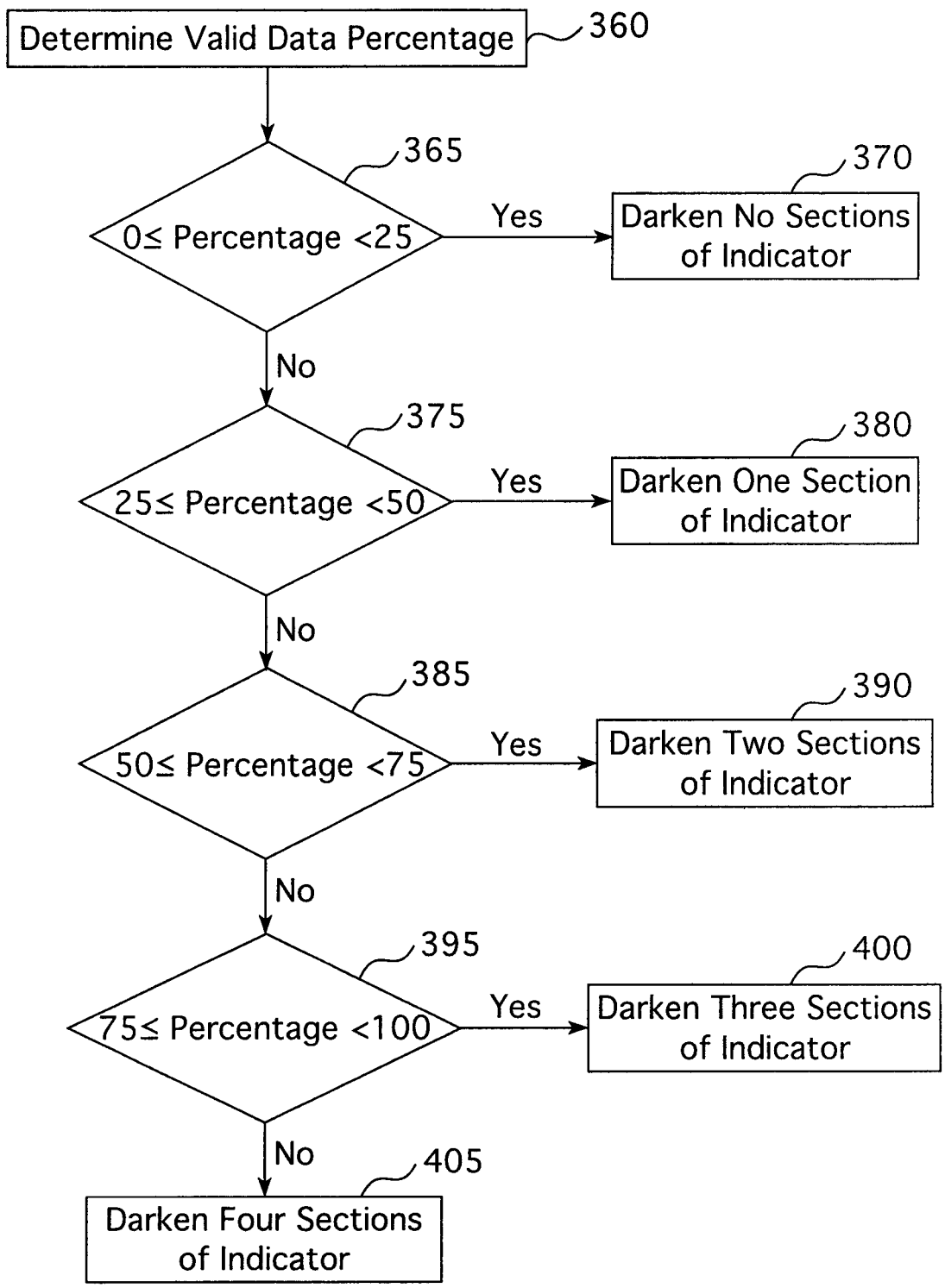
FIG. 11 is a flowchart showing a method of determining and displaying the particular status indicator 235 shown in FIGS. 9A through 9D according to one particular embodiment.

FIG. 11 is a flowchart showing a method of determining and displaying the particular status indicator 235 shown in FIGS. 9A through 9D according to one particular embodiment. Referring to FIG. 11, the method begins at step 360, wherein a valid data percentage is determined. This percentage is determined by dividing the current accumulated valid data time variable (step 340 in FIG. 10) by the amount of valid data required for a valid study (step 300 in FIG. 10) and multiplying the quotient by 100. For example, if four hours of valid data has been collected as indicated by the current value of the accumulated valid data time variable, and the amount of valid data required for a valid study is eight hours, then the percentage calculated at step 360 would be 50 percent.

Following step 360, a determination is made at step 365 as to whether the determined percentage is greater than or equal to zero and less than 25. If the answer is yes, then, at step 370, no sections of the status indicator 235 are darkened. If the answer at step 365 is no, the method proceeds to step 375, wherein a determination is made as to whether the determined percentage is greater than or equal to 25 but less than 50. If the answer is yes, then, at step 380, one section of the status indicator 235 is darkened. If the answer at step 375 is no, then the method proceeds to step 385, wherein a determination is made as to whether the determined percentage is greater than or equal to 50 but less than 75. If the answer is yes, then at step 390, two sections of the status indicator 235 are darkened. If the answer at step 385 is no, then the method proceeds to step 395, wherein a determination is made as to whether the determined percentage is greater than or equal to 75 but less than 100. If the answer is yes, then at step 400, three sections of the status indicator 235 are darkened. If, however, the answer at step 395 is no, then than means that the determined percentage is equal to 100 percent or more, and the method proceeds to step 405, wherein all four sections of status indicator 235 are darkened, thereby indicating that a sleep study with sufficient valid data has been completed.

One particular non-limiting implementation for determining whether flow data is valid is as follows. Initially, the flow data status is set to "Bad." Whenever the flow data status is classified as "Bad", the peak-to-peak value of the current flow data sample is compared to some predetermined threshold value. If the peak-to-peak value is greater than that threshold value, then the flow data status is set to "Good." If the peak-to-peak value is less than or equal to that threshold value, then the flow data status remains set to "Bad." Whenever the flow data status is classified as "Good," the peak-to-peak value of the then current flow data sample is compared to the predetermined threshold value at one second intervals. During some initial predetermined setup period of the sleep study (e.g., the first 15 minutes), the flow data status will then be changed from "Good" to "Bad" if the peak-to-peak value of the then current flow data sample is determined to be less than or equal to the threshold value six consecutive times (i.e., for six seconds). After the initial predetermined setup period of the sleep study, the flow data status will then be changed from "Good" to "Bad" if the peak-to-peak value of the then current flow data sample is determined to be less than or equal to the threshold value 90 consecutive times (i.e., for 90 seconds). The "Good" or "Bad" status is used in step 325 of FIG. 10.

The invention thus provides a data recorder that is adapted to collect various sleep-related parameters from the patient for a sleep study and provide a status indicator to the patient which indicates the amount of valid sleep study data that has been collected by the data recorder, preferably as compared to some predetermined amount of valid data that is required in order to deem the study valid. A patient will therefore be able to determine whether or not sufficient valid data has been recorded and make an informed decision as to whether the data recorder should be returned to the clinician supervising the sleep study or kept for additional data collection. As a result, wasted trips to the clinician can be avoided.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An apparatus for collecting data for a sleep study, comprising:
    a sensor adapted to collect data relating to a parameter of a user of the apparatus over a period of time; and
    a controller operatively coupled to the sensor, the controller being adapted to:
    (a) receive configuration information specifying a predetermined amount of valid data that is required for a sleep study to be deemed valid,
    (b) receive the data relating to the parameter and determine an amount of the received data that is valid, and
    (c) cause a study status indicator to be output by the apparatus that is based on the amount of the received data that is determined to be valid and the predetermined amount specified in the configuration information and that indicates how much valid data has been collected as compared to the predetermined amount of valid data.

2. The apparatus according to claim 1, wherein the study status indicator is representative of a percentage based on the amount of the received data that is determined to be valid as compared to the predetermined amount specified in the configuration information.

3. The apparatus according to claim 2, wherein the study status indicator is a visual indicator.

4. The apparatus according to claim 3, wherein the visual indicator comprises a plurality of sections, wherein at least one section in the plurality of sections is visually distinguished from a remainder of the plurality of sections based on the percentage.

5. The apparatus according to claim 1, wherein the sensor comprises:
   a flow sensor adapted to collect flow data relating to a flow of gas breathed in and out by the user; and further comprising an oximetry sensor adapted to collect oximetry data relating to an oxygen saturation of the user, the data relating to the parameter comprising the flow data and the oximetry data, wherein the controller is adapted to determine an amount of the received data that is valid by determining an accumulated time during which the flow data and the oximetry data are simultaneously valid.

6. The apparatus according to claim 5, wherein the status indicator is representative of a percentage based on the amount of the received data that is determined to be valid as compared to the predetermined amount specified in the configuration information.

7. The apparatus according to claim 6, wherein the status indicator is a visual indicator.

8. The apparatus according to claim 7, wherein the visual indicator comprises a plurality of sections, wherein at least one section in the plurality of sections is visually distinguished from a remainder of the plurality of sections based on the percentage.

9. The apparatus according to claim 5, wherein the oximetry sensor comprises an SpO2 probe.

10. The apparatus according to claim 5, wherein the flow sensor comprises:
    a temperature sensor adapted to collect the flow data based on a temperature of the gas breathed in and out by the user;
    a pressure transducer adapted to collect the flow data based on pressure variations of the gas breathed in and out by the user; or
    both the temperature sensor and the pressure transducer.

11. The apparatus according to claim 5, wherein the flow data is deemed to be valid responsive to a peak-to-peak change in the flow data exceeding a predetermined threshold.

12. The apparatus according to claim 5, wherein portions of the flow data and the oximetry data are deemed to be simultaneously valid during time periods where both the flow data and the oximetry data are valid for at least a predetermined amount of time.

13. The apparatus according to claim 12, wherein the predetermined amount of time is at least one minute.

14. A method of collecting data for a sleep study using an apparatus having one or more sensors for collecting the data, comprising:
    receiving on the apparatus configuration information specifying a predetermined amount of valid data that is required for a sleep study to be deemed valid;
    collecting with the one or more sensors data relating to a parameter of a patient over a period of time;
    determining on the apparatus an amount of the collected data that is valid;
    storing on the apparatus at least the collected data that is determined to be valid; and
    providing a study status indicator that is based on the amount of the collected data that is determined to be valid and the predetermined amount specified in the configuration information and that indicates how much valid data has been collected as compared to the predetermined amount of valid data.

15. The method according to claim 14, wherein the study status indicator is representative of a percentage based on the amount of the collected data that is determined to be valid as compared to the predetermined amount specified in the configuration information.

16. The method according to claim 15, wherein the study status indicator is a visual indicator.

17. The method according to claim 16, wherein the visual indicator comprises a plurality of sections, wherein at least one section in the plurality of sections is visually distinguished from a remainder of the plurality of sections based on the percentage.

18. The method according to claim 14, wherein the collecting data relating to the parameter comprises:
    collecting flow data relating to a flow of gas breathed in and out by the user; and
    collecting oximetry data relating to an oxygen saturation of the user, the data relating to the parameter comprising the flow data and the oximetry data, and wherein the determining an amount of the collected data that is valid comprises determining an accumulated time during which the flow data and the oximetry data are simultaneously valid.

19. The method according to claim 18, wherein the study status indicator is representative of a percentage based on the amount of the collected data that is determined to be valid as compared to the predetermined amount specified in the configuration information.

20. The method according to claim 19, wherein the study status indicator is a visual indicator.

21. The method according to claim 20, wherein the visual indicator comprises a plurality of sections, wherein at least one section in the plurality of sections is visually distinguished from a remainder of the plurality of sections based on the percentage.

22. The method according to claim 18, wherein the flow data is deemed to be valid responsive to peak-to-peak changes in the flow data exceeding a predetermined threshold.

23. The method according to claim 18, wherein portions of the flow data and the oximetry data are deemed to be simultaneously valid during time periods where both the flow data and the oximetry data are valid for at least a predetermined amount of time.

24. The method according to claim 23, wherein the predetermined amount of time is at least one minute.

25. The method according to claim 14, wherein the receiving, collecting, determining, storing, and providing steps are repeated one or more times using the apparatus.

* * * * *